United States Patent
Sandrin et al.

(10) Patent No.: US 12,376,829 B2
(45) Date of Patent: Aug. 5, 2025

(54) ELASTOGRAPHY DEVICE AND METHOD

(71) Applicant: ECHOSENS, Paris (FR)

(72) Inventors: Laurent Sandrin, Bourg-la-Reine (FR); Stéphane Audiere, Paris (FR)

(73) Assignee: ECHOSENS, Paris (FR)

( * ) Notice: Subject to any disclaimer, the term of this patent is extended or adjusted under 35 U.S.C. 154(b) by 97 days.

(21) Appl. No.: 18/349,630

(22) Filed: Jul. 10, 2023

(65) Prior Publication Data
US 2023/0346350 A1    Nov. 2, 2023

Related U.S. Application Data

(63) Continuation of application No. 17/371,790, filed on Jul. 9, 2021, now Pat. No. 11,872,082.

(51) Int. Cl.
*A61B 8/00*    (2006.01)
*A61B 8/08*    (2006.01)

(52) U.S. Cl.
CPC ............... *A61B 8/485* (2013.01); *A61B 8/42* (2013.01); *A61B 8/4444* (2013.01);
(Continued)

(58) Field of Classification Search
CPC ......... A61B 8/485; A61B 8/42; A61B 8/4444; A61B 8/4477; A61B 8/4483;
(Continued)

(56) References Cited

U.S. PATENT DOCUMENTS

| 6,770,033 B1 | 8/2004 | Fink et al. |
| 2005/0203398 A1* | 9/2005 | Sandrin ............... A61B 5/0051 600/438 |

(Continued)

FOREIGN PATENT DOCUMENTS

EP    3 769 691 A1    1/2021

OTHER PUBLICATIONS

Lorée, H., et al., "Vibration-Guided Transient Elastography: a Novel Fibroscan® Examination With Improved Guidance for Liver Stiffness Measurement," Ultrasounds in Med. & Biol., vol. 46, No. 9, (2020), pp. 2193-2206.
(Continued)

*Primary Examiner* — Alexei Bykhovski
(74) *Attorney, Agent, or Firm* — Pillsbury Winthrop Shaw Pittman LLP

(57) ABSTRACT

An elastography device includes a probe, to be held against the body of a subject, the probe including a single ultrasound transducer; or a plurality of ultrasound transducers, all ultrasound transducers of the being motionless with respect to each other, and a low frequency vibrator, arranged to induce a displacement of said single ultrasound transducer or plurality of ultrasound transducers towards a tissue to be characterized, and an electronic unit including an electronic circuit, configured to control the single ultrasound transducer or plurality of ultrasound transducers to emit a sequence of ultrasound pulses in the tissue to be characterized, and configured to acquire echo signals received by the single ultrasound transducer or plurality of ultrasound transducers in response to the ultrasound pulses emitted, in order to track how elastic waves travel in the tissue.

20 Claims, 10 Drawing Sheets

(52) U.S. Cl.
CPC .......... *A61B 8/4477* (2013.01); *A61B 8/4483* (2013.01); *A61B 8/5207* (2013.01); *A61B 2562/0219* (2013.01)

(58) Field of Classification Search
CPC .......... A61B 8/5207; A61B 2562/0219; A61B 8/4494; A61B 8/085
See application file for complete search history.

(56) References Cited

U.S. PATENT DOCUMENTS

| | | | | |
|---|---|---|---|---|
| 2009/0099448 | A1* | 4/2009 | Sandrin | A61B 5/0051 |
| | | | | 600/438 |
| 2013/0090591 | A1* | 4/2013 | Ferrara | A61P 35/00 |
| | | | | 604/20 |
| 2013/0197401 | A1* | 8/2013 | Sato | A61N 7/00 |
| | | | | 601/2 |
| 2014/0276055 | A1* | 9/2014 | Barthe | A61B 8/4466 |
| | | | | 600/439 |
| 2019/0125300 | A1 | 5/2019 | Kong et al. | |
| 2020/0029934 | A1 | 1/2020 | Sandrin | |

OTHER PUBLICATIONS

Sandrin, L., et al., "Shear Elasticity Probe for Soft Tissues with 1-D Transient Elastography," IEEE Transactions on Ultrasonics, Ferroelectrics, and Frequency Control, vol. 49, No. 4, Apr. 2002, pp. 436-446.
Extended European Search Report as issued in European Patent Application No. 21305956.1, dated Jan. 7, 2022.

* cited by examiner

ELASTOGRAPHY DEVICE AND METHOD

CROSS-REFERENCE TO RELATED APPLICATIONS

This application is the continuation of U.S. application Ser. No. 17/371,790, filed Jul. 9, 2021. The content of this application is incorporated herein by reference in its entirety.

FIELD

The disclosed technology concerns an elastography device and method. It concerns more particularly such a device arranged:
- to generate an elastic wave that travels in a tissue to be characterized, by moving a tip that is in contact with said tissue,
- to transmit ultrasound pulses and to receive corresponding echoes, to track how this elastic wave travels in this tissue, in order to characterize the tissue stiffness.

BACKGROUND

Liver stiffness, measured for instance by Vibration-Controlled Transient Elastography, has been shown to be a very useful tool to help health care professionals to detect or to characterize liver disease or damages, and more generally to monitor the condition of the liver of a subject. FIG. 1 schematically represents an elastography device 1a of the prior art, that is adapted to measure liver stiffness by Vibration-Controlled Transient Elastography. This device comprises a probe 2a with:
- a casing 3a, to be handheld;
- a tip 4a, that can be moved relative to the casing 3a by a low frequency vibrator 5a; and
- an ultrasound transducer 6a, mounted at an end of the tip 4a (possibly with a sealing membrane covering the ultrasound transducer).

During measurement, the probe casing 3a is handheld in such a way that the ultrasound transducer 6a is slightly pressed against the body 8 of the subject under examination. A transient displacement of the tip 4a is then triggered, causing the ultrasound transducer 6a to move towards the body of the subject, and back, thereby generating low frequency elastic waves (and, in particular, a low frequency shear wave) in the tissue. The corresponding displacement d(t) of the ultrasound transducer 6a is schematically represented over time t in FIG. 2. d(t) corresponds more precisely to the position of the transducer 6a along an axis z directed towards the subject's body (see FIG. 1), at time t, relative to an initial position of the transducer 6a (which is its position just before triggering this transient vibration). As represented in FIG. 2, a sequence S of ultrasound pulses USP, starting when the low frequency vibration is triggered, is emitted by the ultrasound transducer 6a. These ultrasound pulses enable to track how elastic waves, induced in the tissue facing the probe, travel in this tissue. To this end, two echo signals, corresponding to two successive ultrasound shots of this sequence, are correlated together to determine, for different depths in the tissue, the distance over which the tissue has moved between these two pulses.

At each time, a strain map (sometimes called elastogram or displacements or shear wave propagation map) in the tissue is thus determined as a function of the depth z in this tissue. FIG. 3 represents, as a function of time t and depth z, the strain map in the liver of a subject that results from imparting a low frequency vibration such as the one represented in FIG. 2. This spatio-temporal representation of the elastic waves propagating in the tissue under examination is called an elastogram. It enables one to visualize very clearly how such waves propagates in the tissue. The speed of propagation of shear waves in this tissue can be determined from the slope of the straight line represented in this figure, which shows the position of the wavefront as a function of time and depth. The tissue stiffness is then deduced from this speed of propagation.

When analyzing and processing the echo signals recorded during such a measurement process, it is desirable to compensate for the displacement d(t) of the ultrasound transducer 6a. Indeed, in such a device, the ultrasound transducer 6a is fixed on the moving tip 4a itself. So, when the tip 4a moves, the distance between the transducer 6a and such or such part of the tissue varies. With no correction, the apparent depth, at which such or such strain would be observed would thus be slightly different from the depth at which this strain actually occurs.

Besides, for a couple of two successive shots emitted to determine the strain in the tissue at a given time (by correlating the two corresponding echo signals), the displacement of the ultrasound transducer between these two pulses results in an apparent overall displacement of the whole tissue, superimposed to the actual tissue displacement caused by the elastic waves travelling in it. This offset, which is the same for each depth, can be readily suppressed by computing the z-derivative of the tissue displacement determined at the time considered, as explained in section III.A (p. 440) of the following article: "Shear elasticity probe for soft tissues with 1-D transient elastography," L. Sandrin et al., *IEEE Transactions on Ultrasonics, Ferroelectrics, and Frequency Control*, vol. 49, no. 4, pp. 436-446, April 2002. Still, as explained in this article, it is highly desirable to compensate for the transducer's displacement before correlating the two echo signals recorded. Indeed, with no compensation of the transducer's movement, the displacement measured by correlation is significantly larger, and thus noise and more time consuming to determine.

To compensate for the transducer's displacement d(t) prior to carrying out echo signals correlation, the following technique is usually employed. The sequence of ultrasound pulses S is emitted, and the echo signals received in response are recorded, as explained above. These echo signals are then post-processed by a central electronic unit 7a, that has the structure of a computer and is operatively connected to the probe 2a. This post-processing, described for instance in the article mentioned above, comprises:
a) estimating the transducer's displacement d(t) from the echo signals themselves;
b) for each echo signal, compensating for the displacement d(t) of the transducer (that has been estimated in step a)), in the frequency domain, by multiplying the Fourier transform of this echo signal by $\exp(j2\pi f \Delta t)$, where f is the frequency and where $\Delta t$ is equal to $2 \cdot d/v_{us}$, $v_{us}$ being the speed of ultrasound in the tissue;
c) correlating the echo signals, to determine the tissue displacement as a function of depth z, for each time t;
d) optionally, computing the z-derivative $\partial^*/\partial z$ of the spatio-temporal displacement map obtained in step c).

In step a), the transducer's displacement d(t) can be estimated by identifying, in each echo signal a strong back-reflection associated to element assumed to have a fixed position in tissue. It could be estimated also assuming that the displacement of the tissue, very deep in it, is negligible, and that the displacement observed deep in the tissue corresponds in fact to the transducer's displacement between two pulses.

This procedure is generally satisfactory. Still, the inventors have noticed that step a) may fail, for some of the echo signals recorded, thus providing an incorrect value for the transducers' displacement d(t) for the echo signals in question. These echo signals are thus incorrectly re-aligned, resulting in a few noisy, disruptive columns impairing the elastogram finally obtain. Besides, this procedure requires a lot of computing resources, in terms of storage, data transfer and computation, thus limiting the pulse repetition rate of the ultrasound pulses. This constraint is even more limiting in the case of Vibration-Controlled Harmonic Elastography, for which a vibration (for instance a sinusoidal vibration), is exerted repeatedly, continuously on the tissue to be characterized, while the deformation of the tissue caused by this vibration is monitored in real time.

SUMMARY

To resolve at least partially the problems mentioned above, an elastography device is provided, the elastography device comprising:
- a probe, to be held against the body of a subject, the probe comprising:
  - a single ultrasound transducer; or a plurality of ultrasound transducers, all ultrasound transducers of the probe that are arranged to emit ultrasound pulses in a tissue to be characterized being motionless with respect to each other, and
  - a low frequency vibrator, arranged to induce a displacement of said single ultrasound transducer or plurality of ultrasound transducers towards said tissue, and
- an electronic unit, configured to control the single ultrasound transducer or plurality of ultrasound transducers to emit a sequence of ultrasound pulses, and configured to acquire echo signals received by the single ultrasound transducer or plurality of ultrasound transducers in response to the ultrasound pulses emitted, in order to track how elastic waves, induced in the tissue by the displacement of the single ultrasound transducer or the plurality of ultrasound transducers, travel in said tissue,
the electronic unit being further configured to generate, for one or more of the ultrasound pulses emitted:
  - a temporal offset upon emission, by which the emission of an ultrasound pulse is shifted,
  - and/or a temporal offset upon reception, by which an echo signal acquired in response to said emitted ultrasound pulse is shifted,
  so as to compensate for a temporal shift of said echo signal with respect to other echo signals acquired, caused by the displacement of the ultrasound transducer or plurality of ultrasound transducers occurring during said sequence of ultrasound pulses,
  the temporal offset upon emission and/or the temporal offset upon reception being adjusted so that a difference thereof varies as a function of $2 \cdot d / v_{us}$, where d is the displacement of the single transducer or plurality of ultrasound transducers at the time of emission, and where $v_{us}$ is the speed of ultrasound in said tissue.

The emissions of the ultrasound pulses in question are shifted temporally by said temporal offset upon emission, by delaying these emissions in a controlled manner, for instance using a controllable delay connected upstream of an ultrasound pulser of the probe. In other words, this temporal shift is achieved in the temporal domain, upon emission.

Each echo signal is formed by a signal, received over time by the transducer after the emission of the pulse in question. It is more precisely the signal received within a given temporal window (see FIG. 4 for example) starting after this emission and having a given duration (for instance, a duration of 100 μs, if one wants to explore the tissue over a depth of 7.5 cm, should the speed of ultrasound $v_{us}$ be 1.5 mm/μs). In practice, the signal received within this temporal window, and which forms the echo signal in question, is recorded, or, in other words, written in a memory of the probe. The temporal offset upon reception is obtained by shifting the beginning of this temporal window (which may be an acquisition and recording temporal window, as explained above). Anyhow, this temporal shift is achieved in the temporal domain, here.

In the elastography device presented above, the temporal shifts between the different echo signals, due to the movement of the ultrasound transducer or plurality of ultrasound transducers during the measurement, are compensated at the outset, upon emission and/or right upon reception, in real time, that is before recording the echo signals or transferring them to a remote computing unit. This compensation scheme substantially reduces the computation burden, compared to the post-processing method presented above in the background section. As a result, the disclosed compensation scheme improves operation of the computation unit of the elastography device.

The displacement d(t) of the transducer or plurality of transducers may be measured directly by a displacement sensor fitted to the probe. It may also be deduced from a command signal controlling the vibrator, the displacement induced by the vibrator being controlled by means of a displacement sensor and a control-loop (implemented by a control-loop electronic circuit) so that it matches this command signal. Anyhow, in this device, the displacement d(t), or at least a signal representative of it, is readily available, and it is not necessary to determine it by post-processing the echo signals themselves. Again, this substantially reduces the computation burden, compared to the post-processing method presented above in the background section. Besides, issues associated with a possible failure of the estimation of the displacement d from the echo signals themselves (i.e.: possible failure of step a) above), are avoided, in the disclosed device.

In the disclosed device, echo signals can be temporally re-aligned with each-other, directly at the ultrasound sequencer and ultrasound receiver level (because the complex post-processing procedure mentioned above is no longer necessary). Because re-aligned echo signals are thus available just downstream the ultrasound receiver, the correlation computation between successive echo signals can be achieved immediately afterwards, by means of a dedicated electronic circuit (such as an adequately programmed FPGA circuit). The quantity of data to be transferred and stored, is thus drastically reduced right from the source, which is very favorable for real-time applications. For example, a typical echo signal may comprise 5000 points of 2 Bytes each (for a typical echo duration of 100 μs and a sampling rate of 50 MHZ), while the corresponding strain line obtained by correlation would comprise around 100 points of 4 bytes each. So, the data volume reduction, operated right at the source, is typically a reduction by a factor of 25, or more. Real-time applications, for which such a data-volume reduction is beneficial, include in particular vibration-controlled harmonic elastography or vibration-guided transient elastography techniques, such as described in the article "Vibration-Guided Transient Elastography: A Novel Fibroscan® Examination with Improved Guidance for Liver Stiffness Measurement" by H. Loree et al., *Ultrasound in Medicine and Biology*, Volume 46, Issue 9, 2020, pp 2193-2206.

Regarding the temporal offsets adjustment, one may note that, when the ultrasound transducer (or plurality of ultrasound transducers) is moved towards the tissue, d being its displacement relative to a reference position (d being positive when the transducer is brought closer to the tissue), then, the time of flight of the ultrasound pulse emitted, for a round-trip towards the part of the tissue to be probed and back, is shorten by the quantity $2 \cdot d/v_{us}$. It is thus desirable to reduce the delay between the emission of the ultrasound pulse, and the acquisition of the corresponding echo signal, as a function of $2 \cdot d/v_{us}$, to obtain an echo signal that remains aligned with the other echo signals in spite of the displacement of the transducer (or plurality of transducers), as illustrated in FIG. 4. It is precisely what is achieved in the disclosed device, by adjusting the temporal offset upon emission and/or the temporal offset upon reception so that a difference thereof varies as a function of $2 \cdot d/v_{us}$.

In particular, the electronic unit of the device may be configured to adjust the temporal offset upon emission and/or the temporal offset upon reception so that the difference between the temporal offset upon reception and the temporal offset upon emission is equal to $\Delta t_0 - 2 \cdot d/v_{us}$, $\Delta t_0$ being a constant delay between the emission of the ultrasound pulse, and the acquisition of the echo signal received in response. By "equal", it is meant equal within a given precision (as an absolute precision is not achievable in practice), for instance equal within a 20% precision (as this enables to remove most of the displacement induced time-shift), or even within a 10% precision, or even better within a 5% precision.

The electronic unit may be configured further to adjust, for the at least some of the ultrasound pulses emitted:
the temporal offset upon emission, so that it is equal to $\delta t_{TX,o} + C \cdot d/v_{us}$, $\delta t_{TX,o}$ being a constant delay upon emission,
and the temporal offset upon reception, so that it is equal to $\delta t_{RX,o} - (2-C) \cdot d/v_{us}$, $\delta t_{RX,o}$, being a constant delay upon reception,
C being a constant coefficient between 0 and 2.

In particular, C may be equal to 1, the temporal offset upon emission, being then equal to $\delta t_{TX,o} + d/v_{us}$, while the temporal offset upon reception is then equal to $\delta t_{RX,o} - d/v_{us}$. In other words, the electronic unit may be configured to distribute evenly the overall time-shift correction to be applied (that is $-2 \cdot d/v_{us}$) between the temporal offset upon emission, and the temporal offset upon reception. This requires dedicated electronics and/or programming than applying the correction only upon emission (with the temporal offset upon emission varying as $2 \cdot d/v_{us}$), or only upon reception (with the temporal offset upon reception varying as $-2 \cdot d/v_{us}$). But in return, it enables an optimally accurate sampling of the deformation of the tissue over time.

Indeed, to probe the tissue displacement δ at depth z and time t, the ultrasound pulse emission should ideally be delayed by $d/v_{us}$, so that the pulse emitted arrives at the position to be probed at the time planned initially, in spite of the transducer(s) displacement d.

Comparatively, if the echo signal received is time-shifted by $-2 \cdot d/v_{us}$ while the emission is not time-shifted, then, the z-shift in the echo signal due to the transducer(s) displacement will be adequately suppressed but the tissue deformation finally obtained will be the one at time $t - d/v_{us}$, not at time t. In other words, the tissue displacement δ obtained by correlating echo signals re-aligned in this way will be the tissue displacement at the actual depth z, with no displacement offset (i.e.: with an adequate z-correction), but with a slight temporal error. In practice, this not-completely-accurate time-sampling of the deformation of the tissue may slightly distort the wavefront, in the elastogram. It is thus desirable to time-shift both the emission and the reception depending on d, as specified above. In this respect, it may be noted that the post-processing compensating technique of the prior art, presented above, does not allow for such an exact time-sampling of the tissue deformation.

As already mentioned, the compensation technique implemented in the instant device requires much less computation than the prior art post-processing technique in question. In particular, it can be done on-the-fly by the ultrasound sequencer implemented in a FPGA.

But in return, this technique requires specific equipment. Indeed, the ultrasound pulser or converter, and/or an electronic module controlling it should enable to time-shift the emission and/or reception, in real time, as a function on a variable input signal (the displacement signal, for instance). And, to the knowledge of the inventors, the ultrasound pulsers or converters and associated control electronics that are commercially available today, generally do not allow for such a control of the delay upon emission/reception, based upon an external signal: they are designed to transmit predetermined (in practice, pre-recorded), fixed sequences of pulses (sequences that can sometimes be quite complex, but are nevertheless predetermined), not sequences adjusted in real time as a function of a variable input signal. Implementing the technique herein disclosed thus required developing such specific electronic modules, which required a substantial development work.

The temporal offset upon emission and/or the temporal offset upon reception are adjusted based on the displacement d of the single transducer or plurality of ultrasound transducers at the time of emission of the ultrasound pulse considered (to compensate adequately the time-shift due to this displacement). Still, it may be noted that a slight temporal margin is tolerated (the displacement d taken into account may be the displacement not exactly at the time of emission of this ultrasound pulse), if only because of the non-zero response time of the displacement sensor and of the electronics controlling the temporal offsets upon emission/reception (small delay usually referred to as "the pipeline time"). For example, for a pulse emitted at time t, the displacement taken into account to shift this pulse (or to shift the corresponding echo signal), may be the displacement at the same time t within a 0.2 ms precision, or with a temporal precision better than 1/30 of the period (or of the typical variation time) of the displacement induced by the low frequency mechanical vibrator.

The electronic unit of the device may comprise electronics for driving/interfacing the probe's actuator(s), transducer(s) and sensor(s), such as amplifiers, pulsers, switches or converters. This electronic unit may comprise also control electronics, for producing adequate control signals, and for processing the signal acquired. These control electronics may comprise one or several electronic logic circuits, including by way of example a microprocessor, a digital signal processor (DSP), a system on a chip, or multiple ones, or combinations of the foregoing. The electronic logic circuit in question may be an FPGA (Field-Programmable Gate Array), for example.

The elastography device presented above may also comprise one or more of the following complementary and non-limiting features, considered individually or according to all technically possible combinations:

The device further comprises a displacement sensor arranged to output a measurement signal representative of the displacement of said single ultrasound transducer or plurality of ultrasound transducers, and wherein the electronic unit is further configured to generate the temporal offset upon emission and/or the temporal offset upon reception based on said measurement signal;

said displacement sensor is an inertial sensor (such as an accelerometer), arranged so that the measurement signal it outputs is representative of the displacement of said single ultrasound transducer or plurality of ultrasound transducers relative to an inertial frame of reference;

the probe comprises a probe casing, to be handheld, and said single ultrasound transducer or plurality of ultrasound transducers is bound to the probe casing with no motion with respect to the probe casing, the vibrator being arranged to move a mass inside the probe casing in order to induce said displacement of the single ultrasound transducer or plurality of ultrasound transducers, towards the body of the subject;

the probe comprises a probe casing, said single ultrasound transducer or plurality of ultrasound transducers being movable with respect to the probe casing, the displacement sensor being arranged so that the measurement signal it delivers is representative of the displacement of said single ultrasound transducer or plurality of ultrasound transducers, relative to the probe casing.

One may note that, when the temporal offset upon emission is adjusted based on the displacement d as explained above, as this displacement varies over time, from one ultrasound pulse to the other, then, the duration between two pulses successively emitted (i.e.: the pulse repetition period) is also modified, depending on the variation of d over time (see FIG. 9, for example). This illustrates that the compensation technique presented above can also be implemented by adjusting the pulse repetition period, based on the variation of d over time.

The instant technology thus concerns also an elastography device comprising:

a probe, to be held against the body of a subject, the probe comprising:
a single ultrasound transducer; or a plurality of ultrasound transducers, all ultrasound transducers of the probe that are arranged to emit ultrasound pulses in a tissue to be characterized being motionless with respect to each other, and
a low frequency vibrator, arranged to induce a displacement of said single ultrasound transducer or plurality of ultrasound transducers towards said tissue, and
an electronic unit, configured to control the single ultrasound transducer or plurality of ultrasound transducers to emit a sequence of ultrasound pulses, and configured to acquire echo signals received by the single ultrasound transducer or plurality of ultrasound transducers in response to the ultrasound pulses emitted, in order to track how elastic waves, induced in the tissue by the displacement of the single ultrasound transducer or the plurality of ultrasound transducers, travel in said tissue,
the electronic unit being further configured so that, for at least some of the ultrasound pulses emitted, a pulse repetition period, that separates an ultrasound pulse from a next ultrasound pulse emitted, varies depending on the displacement of the single ultrasound transducer or plurality of ultrasound transducers, the pulse repetition period:
being shortened compared to a base pulse repetition period To when the single ultrasound transducer or plurality of ultrasound transducers moves away from said tissue,
and being lengthened compared to the base pulse repetition period $T_o$ when the single ultrasound transducer or plurality of ultrasound transducers moves towards said tissue.

In particular, the pulse repetition period may be adjusted based on $v/v_{us}$, where v is the speed of displacement of the single ultrasound transducer or plurality of ultrasound transducers, that is, the time-derivative $d(d)/dt=\dot{d}$ of the displacement d.

One may note that adjusting the pulse repetition period in this way produces the same result, or substantially the same result as adjusting the temporal offset upon emission as a function of $d/v_{us}$. Indeed, adjusting the pulse repetition period in this way is equivalent to adjusting the time-derivative of this offset upon emission depending on the time-derivative of d, instead of adjusting the offset itself based on d.

In particular, the electronic unit may be configured to adjust the pulse repetition period so that it is equal (within a given precision, for instance a 20%, or 10% precision) to $T_o \times (1+v/v_{us}) = T_o \times (1+\dot{d}/v_{us})$, which produces substantially the same temporal shift compensation as adjusting the temporal offset upon emission so that it is equal to $\delta t_{TX,o} + d/v_{us}$.

The electronic unit may also be configured to adjust the pulse repetition period so that it is equal to $T_o \times (1+2 \cdot v/v_{us})$, which corresponds to a case in which the temporal shift to be introduced is entirely introduced upon emission (with no time-shifting upon reception).

More generally, the electronic unit may be configured to adjust the pulse repetition period so that it is equal to $T_o \times (1+C \cdot v/v_{us})$, C being a constant coefficient between 0 and 2.

The instant technology concerns also an elastography method, implemented by means of a device that comprises a probe with:
a single ultrasound transducer; or a plurality of ultrasound transducers, all ultrasound transducers of the probe that are arranged to emit ultrasound pulses in a tissue to be characterized being motionless with respect to each other, and
a low frequency vibrator, arranged to induce a displacement of said ultrasound transducer or plurality of ultrasound transducers towards said tissue,
the method comprising the following steps:
controlling the low frequency vibrator to induce a displacement of said ultrasound transducer or plurality of ultrasound transducers towards said tissue,
controlling said ultrasound transducer or plurality of ultrasound transducers to emit a sequence of ultrasound pulses, and acquiring echo signals received by the ultrasound transducer or plurality of ultrasound transducers in response to the ultrasound pulses emitted, to track how elastic waves, induced in the tissue by the displacement of the ultrasound transducer or plurality of ultrasound transducers, travel in the tissue,
the method further comprising, for one or more of the ultrasound pulses emitted:
generating a temporal offset upon emission, by which the emission of an ultrasound pulse is shifted, and/or generating a temporal offset upon reception, by which an echo signal, acquired in response to the emitted ultrasound pulse is shifted, so as to compensate for a temporal shift of said echo signal with respect to other echo signals acquired, caused by the displacement of the ultrasound transducer or plurality of ultrasound transducers occurring during said sequence of ultrasound pulses, the temporal offset upon emission and/or the temporal offset upon reception being adjusted so that a difference thereof varies as a function of $2 \cdot d/v_{us}$, where d is the displacement of the transducer or plurality of transducers at the time of emission, and where $v_{us}$ is the speed of ultrasound in said tissue The features of the different embodiments of the device described above may apply also to this elastography method.

BRIEF DESCRIPTION OF THE DRAWINGS

Other characteristics and benefits of the disclosed technology will become clear from the description which is given below, by way of example and non-restrictively, in reference to the figures, in which.

DETAILED DESCRIPTION

As mentioned above, the instant technology concerns a vibration-controlled elastography device, that is an elastography device configured:—to generate elastic waves, propagating in a medium to be explored, by moving an element which is in contact with the surface of the medium, such as a probe tip, and—to track how the elastic wave travels in the medium (or, in other words, how the medium is moved by the vibration exerted upon it), by transmitting ultrasound pulses in the medium, and recording echo signals received in response.

The ultrasound pulses and corresponding echo signals are transmitted and received by means of one or more ultrasound transducers, that are fixed on the moving element in question (for instance at an end of the probe's tip), close to or even in contact with the medium to be probed. In the course of an elasticity measurement, these transducers are thus displaced, just as the moving element, which causes a temporal de-alignment of the echo signal acquired, with respect to each others. The elastography device presented here is configured to compensate for the displacement of the ultrasound transducer or transducers, so as to re-align temporally the different echo signals received.

Figure 7:
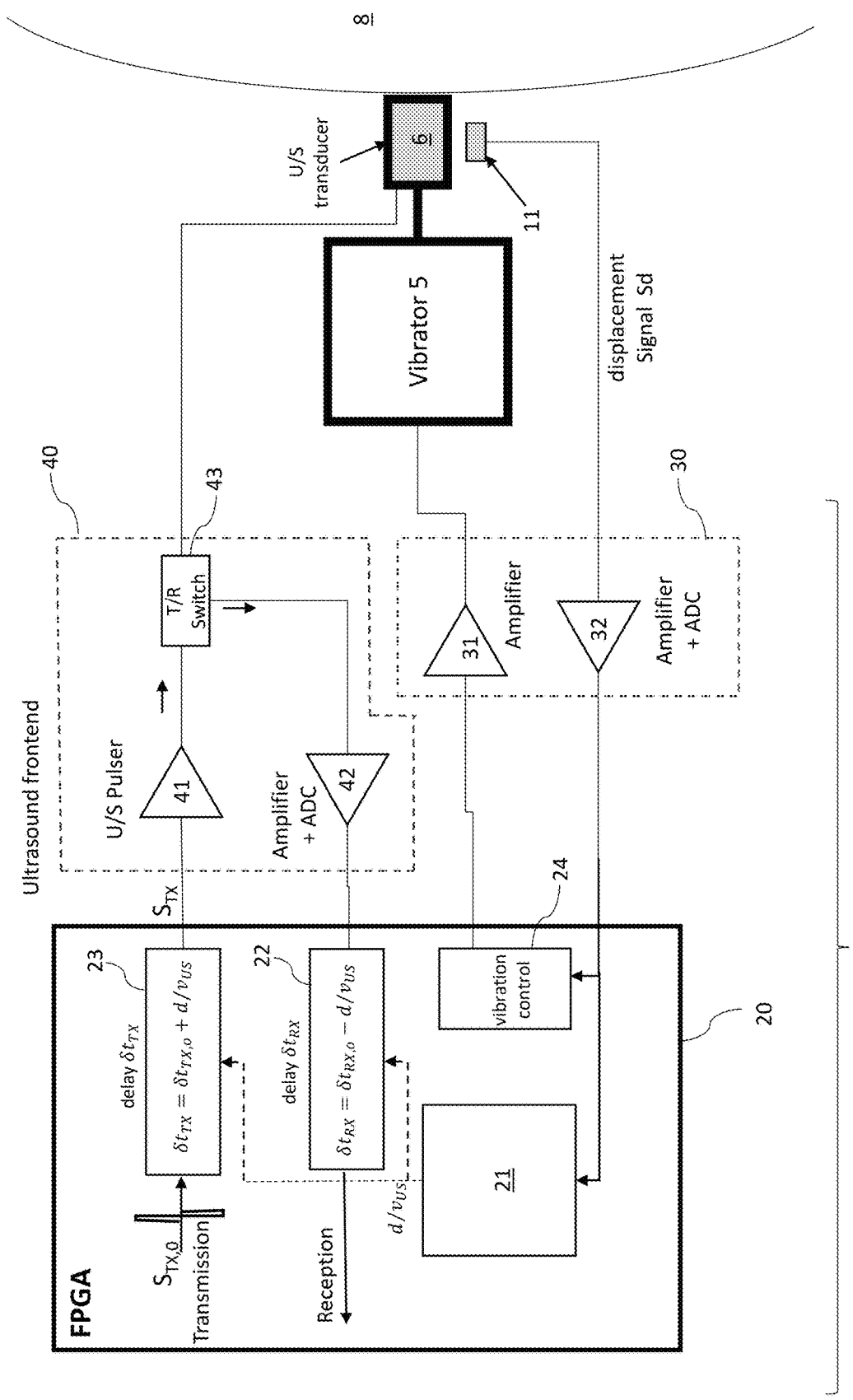
FIG. 7 schematically represents an electronic unit of the device of FIG. 6, as a block diagram.

To this end, temporal offsets upon emission (or, equivalently, a pulse repetition period between successive pulses), and/or temporal offsets upon reception are adjusted in real time, depending on the displacement of the ultrasound transducer or transducers (see FIG. 7, for instance).

Figure 6:
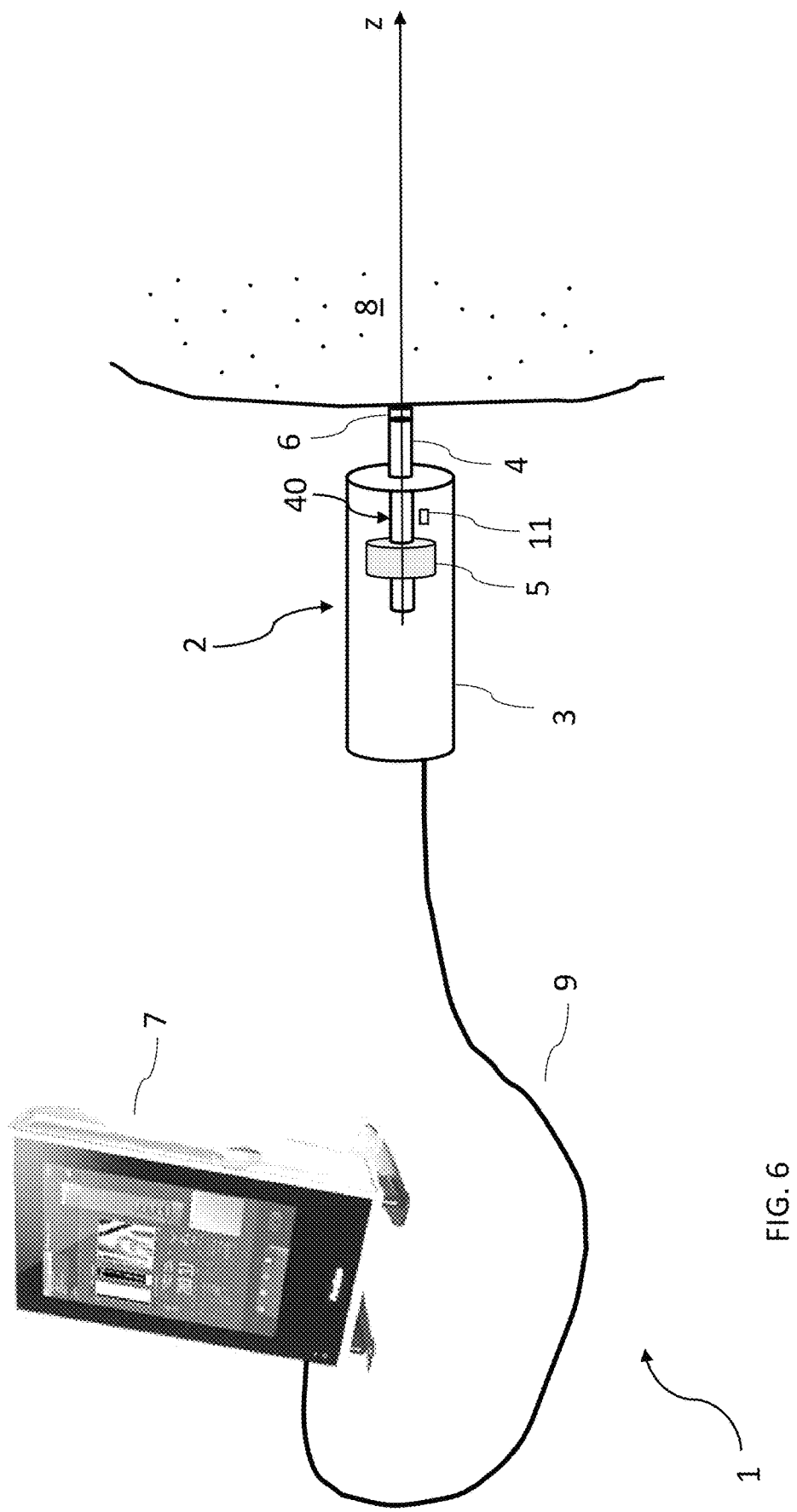
FIG. 6 schematically represents an elastography device according to a first embodiment.
Figure 10:
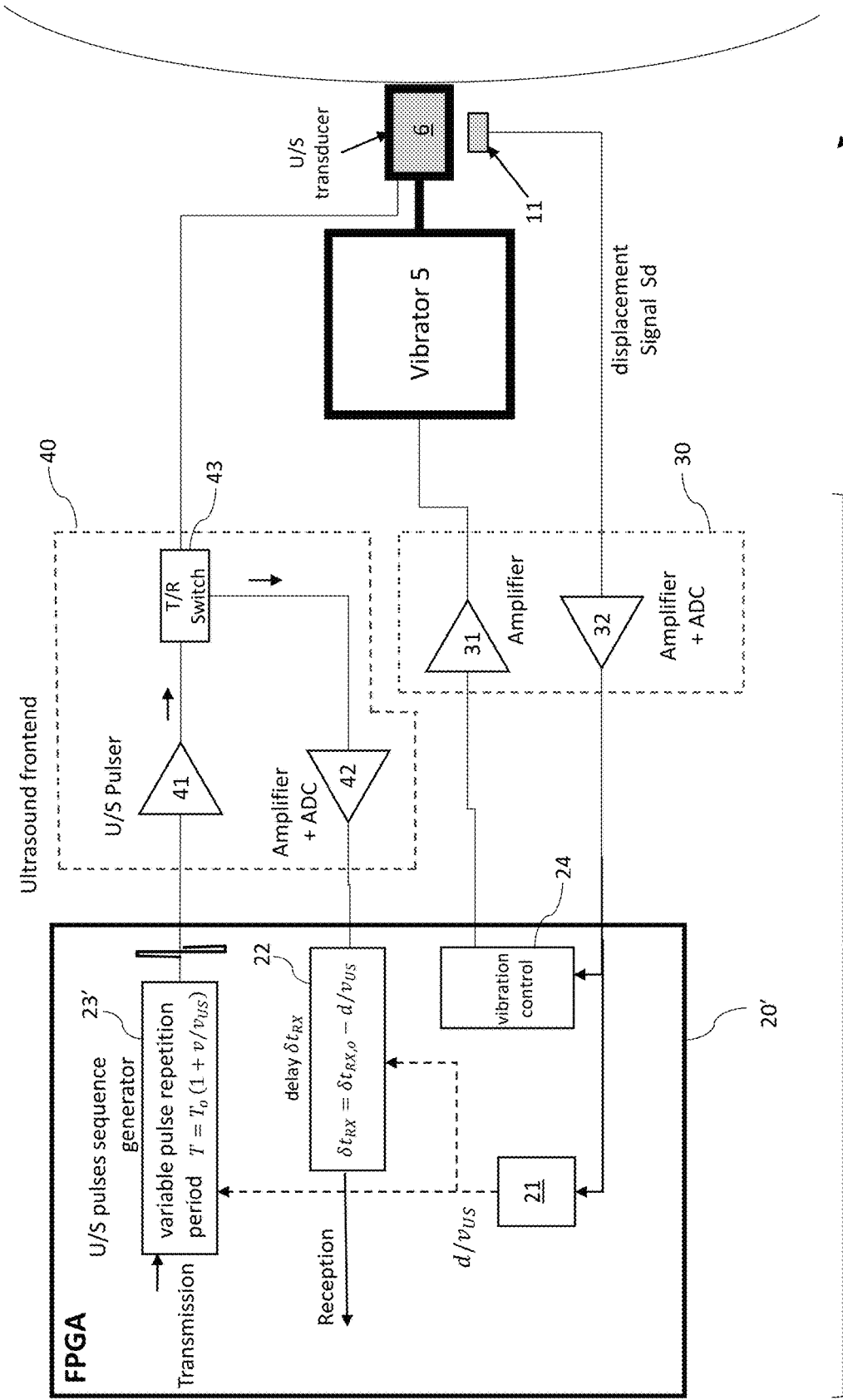
FIG. 10 schematically and partially represents an elastography device according to a second embodiment.
Figure 11:
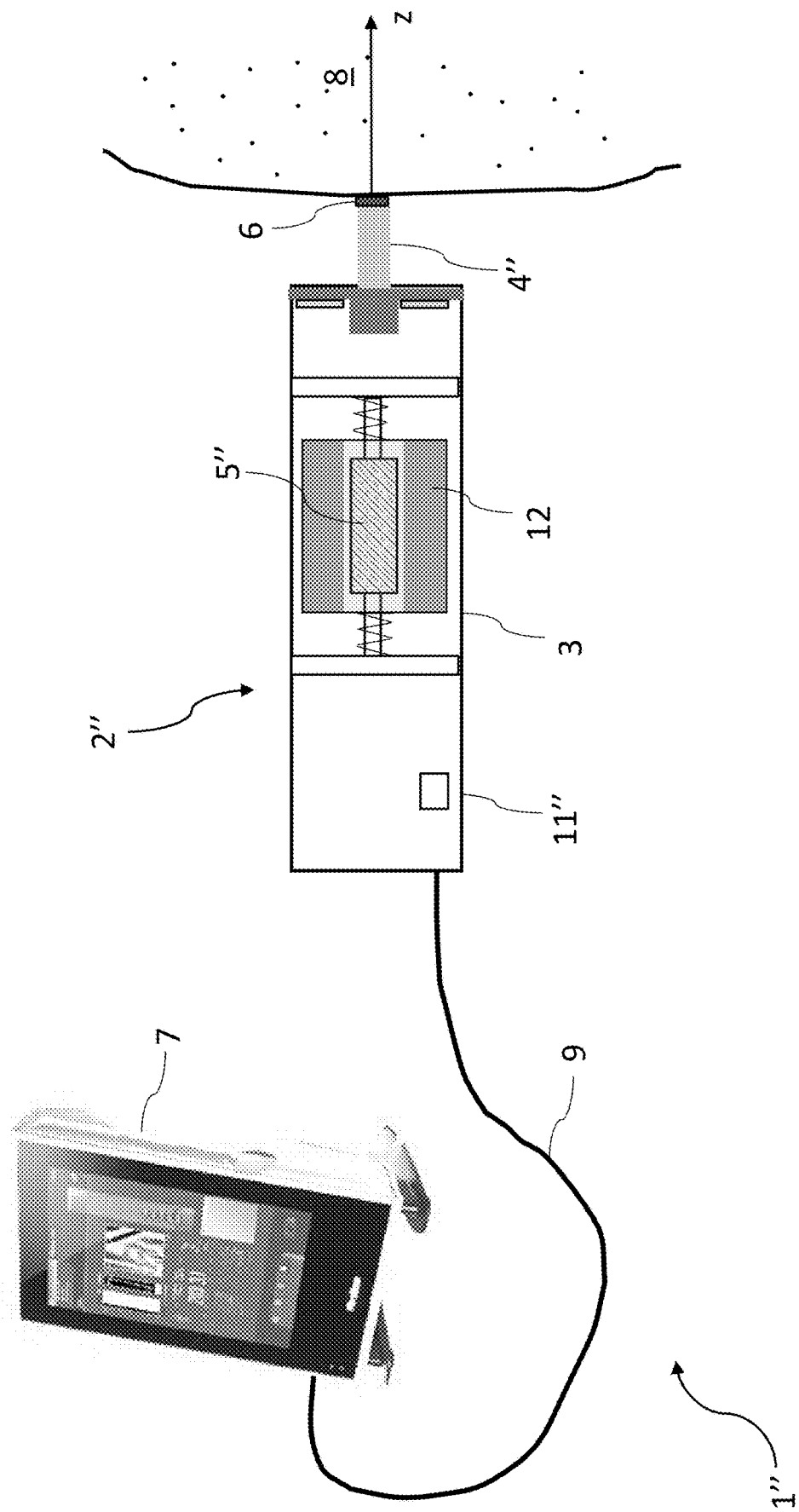
FIG. 11 schematically and partially represents an elastography device according to a third embodiment.

Three embodiments of such a device, respectively identified by the reference numbers 1; 1' and 1", are represented in FIGS. 6, 10 and 11 respectively.

In these three embodiments, the device 1; 1'; 1" comprises a single ultrasound transducer 6. Still, in other embodiments, the elastography device could comprise a plurality of ultrasound transducers. But anyhow, in the device according to the technology disclosed here, all ultrasound transducers that are arranged to emit ultrasound pulses in the tissue to be characterized are motionless with respect to each other. So, they move together, and their motion is characterized by a displacement d which is the same for all the transducers.

The expression "tissue" is understood to mean a part of the body of a subject (either a human or an animal). This expression does not necessarily designate a whole organ or a single organ. The tissue 8, to which mechanical vibrations are delivered and the deformation of which is tracked by the ultrasound pulses, is a part of the subject's body located in the vicinity of the device's probe, along an axis z of the probe. In the following, the abbreviation U/S stands for "ultrasound".

The device 1 according to the first embodiment (FIGS. 6 and 7) is configured to compensate for the time-shifts mentioned above by adjusting a temporal offset upon emission $\delta t_{TX}$, and a temporal offset upon reception $\delta t_{RX}$, depending on the displacement d of the U/S transducer 6.

The device 1' according to the second embodiment is similar to the one of the first embodiment, but it is configured to compensate for the time-shifts in question by adjusting directly a pulse repetition period T between successive U/S pulses, and, optionally, by adjusting also the temporal offsets upon reception $\delta t_{RX}$.

In the devices 1 and 1', the U/S transducer 6 is movable with respect to a casing 3 of the probe 2 of the device. And the probe comprises a low frequency vibrator 5, arranged to move the U/S transducer 6 relative to the casing 3 (casing which is hand-held by an operator), to exert a low frequency vibration on the tissue 8.

By contrast, in the device 1" according to the third embodiment, the U/S transducer 6 is bound to the probe casing 3 with no motion with respect to the probe casing. The probe 2" comprises a vibrator 5" arranged to move a mass 12 inside the probe casing 3 to make the whole probe vibrating.

These three embodiments are however similar to each other, and the identical or corresponding elements of the device 1; 1'; 1" will generally be identified by the same references.

The device 1 according to the first embodiment is now described in more details, with reference to FIGS. 6 to 9.

This elastography device 1 comprises the probe 2, the probe's casing 3, the vibrator 5 and the U/S transducer 6 mentioned above. The U/S transducer 6 is fixed at an end of a tip 4 of the probe, which is actuated by the low frequency vibrator (see FIG. 6).

In this device, the vibrator 5 is rotationally symmetrical around a vibrator axis, which coincide with the probe axis z. When the vibrator 5 vibrates, it induces displacements that are mainly longitudinal, parallel to its axis.

Here, the vibrator 5 is arranged to move a shaft, the end of which forming the tip 4 of the probe. This shaft is centered onto the axis z, and the vibrator 5 is arranged to move this shaft along the axis z. The vibrator 5 is a low frequency vibrator in that it moves the tip with a central, average frequency smaller than 500 hertz, or even smaller than 100 hertz (in contrast with ultrasound shots or echo signals, whose central frequency is typically higher than 1 megahertz, for instance between 1 and 5 megahertz). The vibrator is a low-frequency electro-mechanical actuator, for instance with one or several coils and magnets, similar to a loud-speaker actuator. In an alternative, it may also comprise an electric motor such as a brushless DC motor or an electronically commutated motor. Such an alternative is well adapted to, e.g., vibration-guided transient elastography.

The ultrasound transducer 6 is rotationally symmetrical around a transducer axis and emits ultrasound beams centered on this axis. The transducer axis coincides with the vibrator's axis, and so with the probe axis z. The ultrasound transducer 6 has for instance a circular section, the vibrator's axis passing through the center of this section. This section is small, typically smaller than 1 square centimeters (it may have a diameter smaller than 1 centimeter, or smaller than 8 or even 5 millimeters). The transducer 6 may be covered by a sealing membrane, this sealing membrane being in contact with the subject's body when the probe 2 is held in position, to make a measurement.

Figure 2:
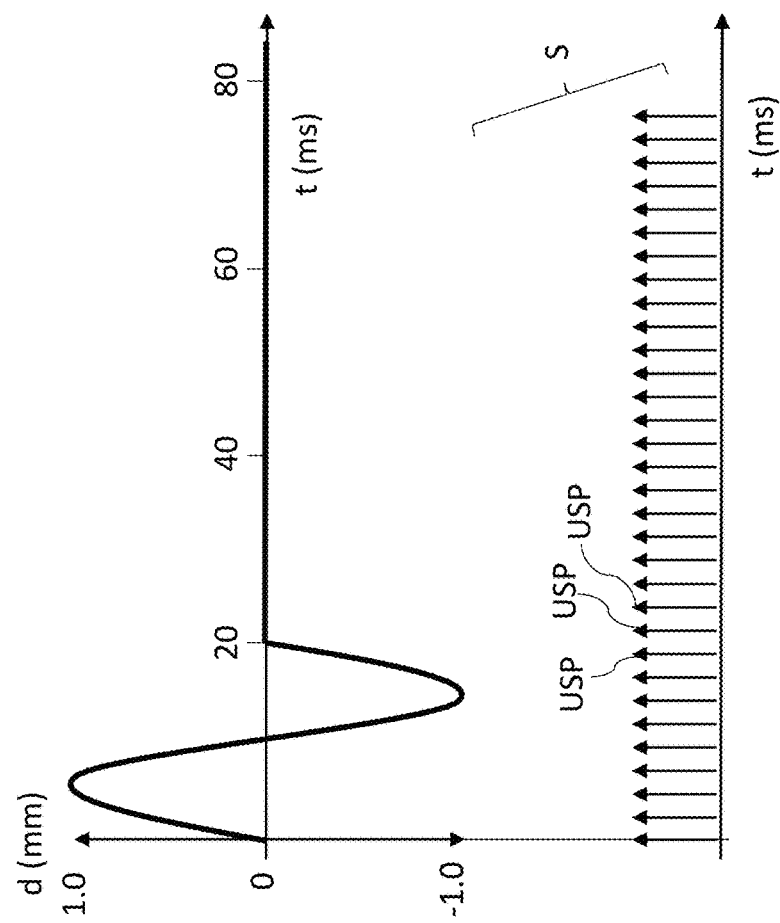
FIG. 2 represents a displacement of the ultrasound transducer of the device of FIG. 1, during a transient elastography measurement, and an ultrasound pulses sequence transmitted during this measurement to track how a tissue is moved in response to this displacement.
Figure 5:
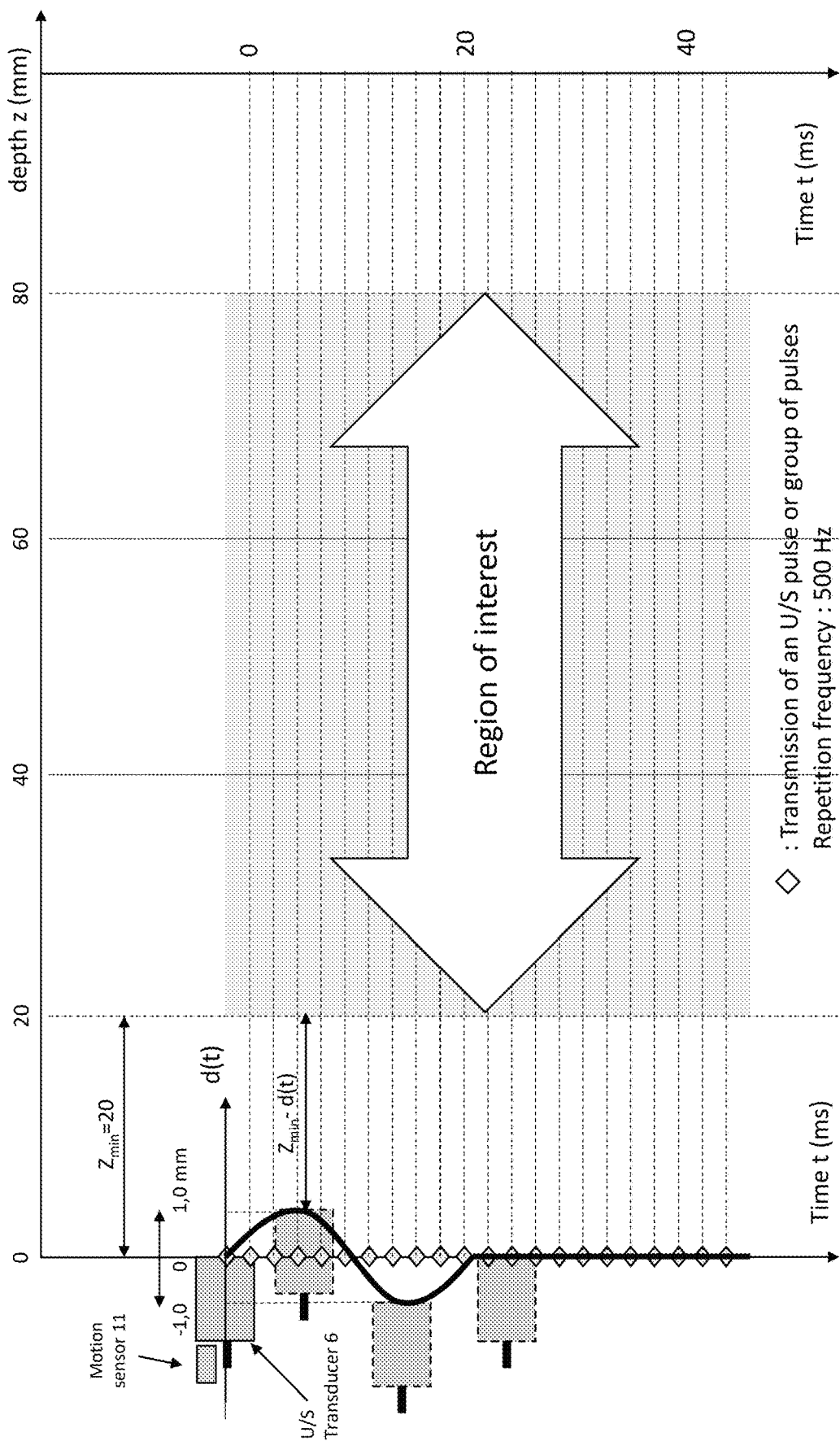
FIG. 5 represents schematically, as a chronogram, the displacement of an ultrasound transducer and times of emission of the ultrasound pulses, during a typical transient elastography measurement.

In practice, the displacement of the ultrasound transducer 6, induced by the vibrator 5, has a peak-to-peak amplitude between 0.1 mm and 10 mm (for instance between 0.5 and 10 mm for the transient elastography measurement in itself, and possibly smaller for a harmonic vibration, employed for instance to guide the operator). In the examples of FIGS. 2 and 5, this amplitude is 2 mm.

The probe 2 comprises a displacement sensor 11, arranged to output a measurement signal $S_d$ representative of the displacement of the ultrasound transducer 6. In this embodiment, the measurement signal $S_d$ is representative of the displacement of the ultrasound transducer 6 relative to the probe casing 3. A part of the displacement sensor 11 is fixed on the shaft mentioned above while another part of the sensor is fitted in the probe, with no motion with respect to the casing 3. The displacement sensor 11 may be a Hall-effect sensor, an induction displacement sensor, an optical sensor comprising a ruler with opaque/transparent alternating zones, or any other suitable sensor.

The probe 2 is operatively connected to a central unit 7, which has the structure of a computer (and that could be a laptop, a smartphone, or a dedicated electronic device arranged to control and to interface the probe, and to process the signals acquired). The central unit comprises at least a memory and a processor. Here, it comprises also a user interface, such as a touch screen. The probe may be connected to the central unit 7 by means of a connection cable 9, or by means of a wireless link.

The device 1 comprises also an electronic unit 10. A block diagram of this electronic unit is represented in FIG. 7.

Some of the elements of this electronic unit 10 (such as the signal conditioning module 32, for instance) can be housed in the probe 2 while other elements of this unit 10 may be part of the central unit 7. Alternatively, the entire electronic unit 10 could be housed in the probe 2, or, on the contrary, it could be entirely integrated into the central unit 7.

As represented in FIG. 7, the electronic unit 10 comprises a control module 20, an ultrasound front end 40, and a motion controller 30 to control the vibrator 5. The ultrasound front end 40 and the motion controller 30 are both connected to the control module 20 (that is to say that they can receive instructions or control signals from the control module 20 or send data or measurement signals to it). The electronic unit comprises also a signal conditioning module 32, to condition and digitalize the measurement signal $S_d$ outputted by the displacement sensor 11. This signal conditioning module 32 is part of the motion controller 30, here.

The motion controller 30 comprises also an amplifier 31, to drive the vibrator 5. The amplifier 31 is configured to convert a control signal into a form suitable to drive the vibrator, from an electrical point of view. The amplifier 31 may thus be a current amplifier or a power amplifier (such as the LM3886 power amplifier by texas instrument, for instance), for instance.

The control module 20 is a device or system comprising electric circuitry for processing data, such as a microprocessor coupled to a non-volatile memory comprising machine executable instructions and/or a programmable microcircuit like an FPGA (field programmable gate array) or another programmable circuit. The control module 20 may also comprise one or several RAM memories or registers. The control module 20 can be in the form of an FPGA carrier board, for instance.

The control module 20 is configured (for instance, programmed via instruction stored in a memory) to control the motion controller 30 in order to displace the shaft 40 (and so, to displace the U/S transducer 6) when an elastography measurement is triggered. This measurement may be triggered manually, by an operator (by means of a push button or a by means of the user interface mentioned above, for instance) or automatically. The shaft displacement is controlled according to a predetermined command signal. Here, this displacement is controlled by means of a control-loop comprising the amplifier 31, the displacement sensor 11, the signal conditioning module 32, and a vibration control module 24, such as a PID corrector (still, in alternative embodiments, the vibrator may be controlled by means of an open loop—that is with no sensor feedback). In the embodiment considered here, the displacement of the shaft induced by the vibrator is a transient displacement, corresponding for instance to one period of a sinusoid having a duration between 5 ms and 50 ms.

The ultrasound front end 40 comprises an ultrasound (U/S) pulser 41, an U/S receiver module 42 and a switch 43 for alternatively transmitting and receiving ultrasonic signals. The U/S pulser 41 comprises an electric circuit configured to generate an electric ultrasonic signal appropriate to drive the U/S transducer 6, based on a transmission control signal $S_{TX}$ outputted by the control module 20. This electric circuit may comprise an amplifier and a digital to analog converter (DAC), for instance an 8 to 16 bits DAC with a 10 to 1000 Mega-sample per second rate. The U/S receiver module 42 comprises an electric circuit configured to acquire an electric ultrasonic signal (an echo signal), previously received by the U/S transducer 6 (and transmitted to the U/S receiver module 42 via the switch 43). The electric circuit of the ultrasonic receiver module 42 may comprise a voltage amplifier, one or more filters and an analog to digital converter (ADC), for instance an 8 to 16 bits ADC with a 10 to 100 Mega-sample per second rate.

The control module 20 is configured (for instance, programmed via instruction stored in a memory) to control the U/S front end 40 so that the U/S transducer 6 emits a sequence of ultrasound pulses USP, such as the sequence S represented in FIG. 2, when the elastography measurement is triggered. The control module 20 is configured also to acquire echo signals received by the U/S transducer 6 in response to the pulses emitted, in order to track how elastic waves, induced in the tissue 8 by the displacement of the U/S transducer 6, travels in the tissue.

The central frequency of each ultrasound pulse USP is comprised for instance between 0.5 and 10 megahertz. The ultrasound pulses of the sequence mentioned above may be transmitted one a time, two successive pulses being separated by a pulse repetition period T, this pulse repetition period being typically between 50 microseconds and 2 milliseconds (which corresponds to a pulse repetition rate between 0.5 kilohertz and 20 kilohertz). The ultrasound pulses of the sequence mentioned above may also be transmitted by groups, for instance by groups of two pulses (to compute correlations between the two corresponding echo signals). The two pulses of each group may be separated by duration between 50 and 200 microseconds, while the groups of pulses themselves are separated by a longer duration, for instance higher than 0.5 ms. It will be appreciated that different transmission sequences can also be considered in various embodiments.

Figure 1:
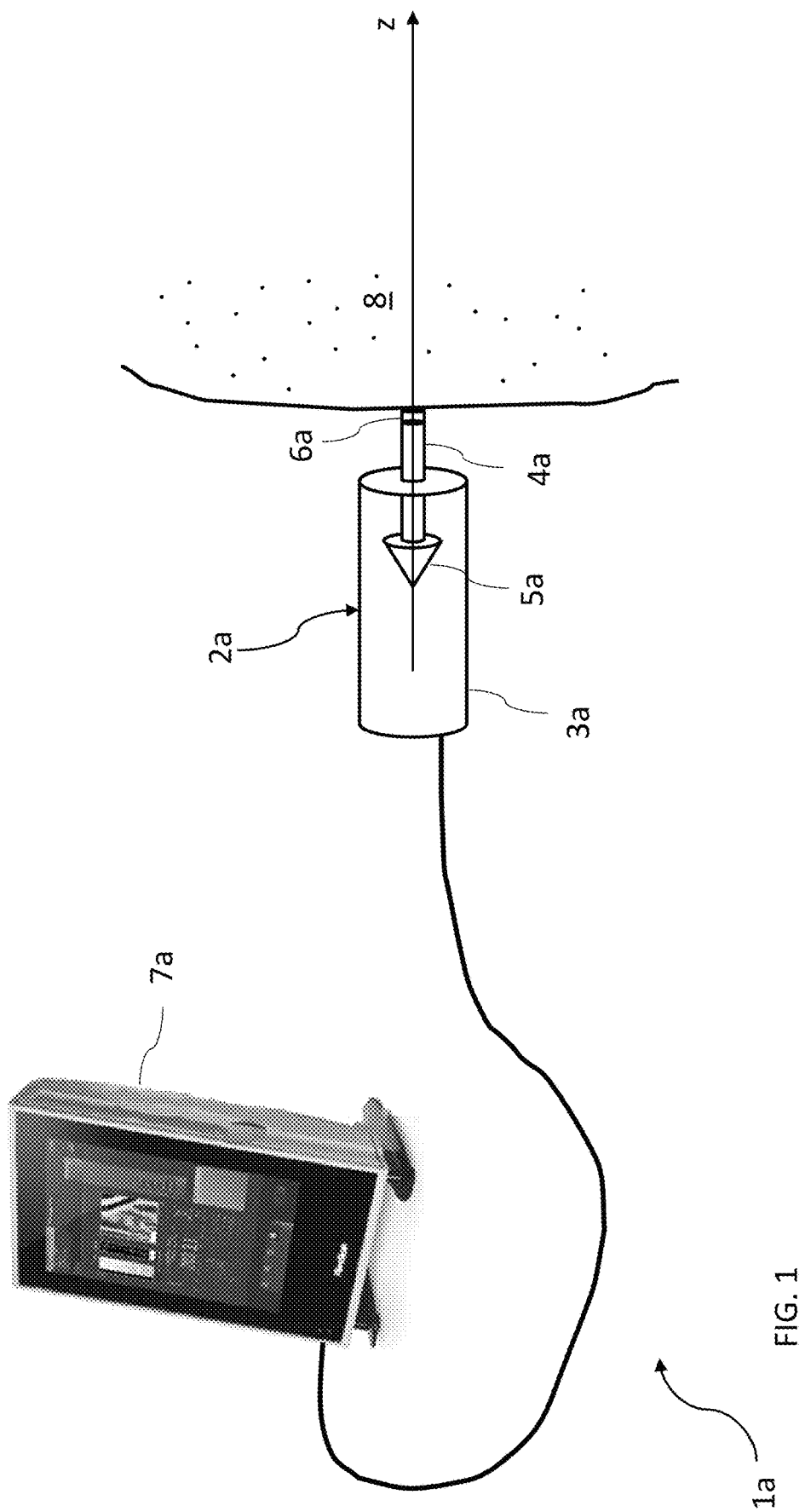
FIG. 1 schematically represents an elastography device of the prior art.
Figure 3:
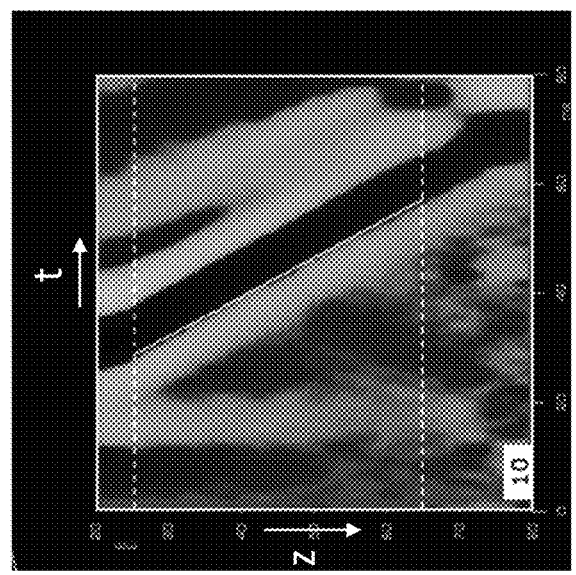
FIG. 3 represents schematically an elastogram obtained by means of the device of FIG. 1.

In the case of Vibration-Controlled Transient Elastography (like in FIGS. 2, 3 and 5), the total duration of this sequence of U/s pulses may be between 50 ms and 200 ms. This duration may be selected depending on the speed of propagation of the elastic wave which is the slower and depending on the depth of the region to be observed. For instance, for an 80 mm depth and a speed of propagation of the 1 m/s (typical for shear waves in the liver of a subject), the sequence may have a duration of 80 ms.

The sequence of U/S pulses transmitted by the device 1 is generated based on a fixed, predetermined reference sequence, by shifting temporally each pulse of the sequence by a temporal offset upon emission $\delta t_{TX}$ which is adjusted in real time depending on the displacement of the U/S transducer 6.

To this end, the control module 20 may generate a reference transmission control signal $S_{TX,O}$ (based on a predetermined transmission sequence stored in a memory of the control module, for instance), when an elastography measurement is triggered, this signal being then delayed in a controlled manner, by means of a controllable delay 23, to produce the transmission control signal $S_{TX}$ sent to the U/S front end 40.

Figure 4:
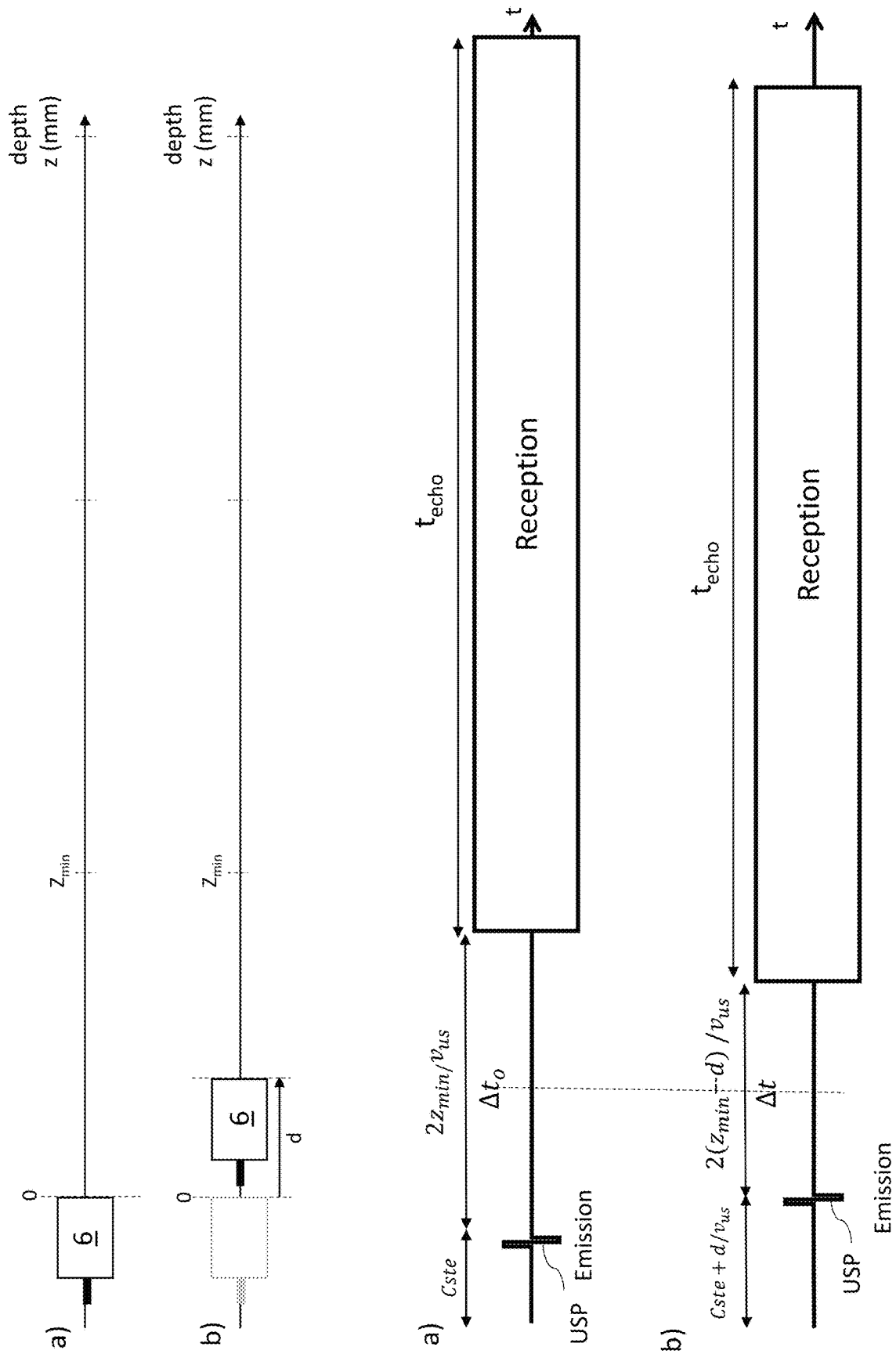
FIG. 4 represents schematically emission and reception times, temporally shifted as a function of a transducer's displacement.

Each echo signal acquired is formed by a signal, received over time t by the U/S transducer 6 after the emission of one of the U/S pulses emitted during said sequence. It is more precisely the signal received within a given temporal window (see FIG. 4) starting after this emission and having a given duration $t_{echo}$. When the U/S transducer 6 does not move, the delay between the U/S pulse emission, and the beginning of this temporal window is $\Delta t_0$. For instance, if the tissue 8 (more generally, the medium to be characterized) is probed, from a minimum depth $z_{min}$, to a maximum depth $z_{max}$, the constant delay $\Delta t_0$ may be set to $2 \cdot z_{min}/v_{us}$, while the window duration $t_{echo}$ is set to $2 \cdot (z_{max}-z_{min})/v_{us}$. For instance, for $z_{min}=20$ mm and $z_{min}=100$ mm (a Region of interest ROI extending from z=20 mm to 80 mm), $\Delta t_0$ and $t_{echo}$ may be set to 27 μs and 107 μs respectively.

The echo signals, received by the U/S transduced 6 in response the U/S pulses transmitted, are shifted temporally, depending on the U/S transducer's displacement. They are shifted by a temporal offset upon reception $\delta t_{RX}$ which varies as a function of the U/S transducer's displacement. More precisely, for each echo signal, the beginning of the temporal window mentioned above is shifted by $\delta t_{RX}$ with respect to a time of reception, initially planned for this pulse supposing there is no displacement of the transducer (in other words, a reference time of reception).

The temporal shift upon reception $\delta t_{RX}$ may be obtained by means of a controllable sequencer 22, selecting the appropriate series of values in a digitalized signal outputted by the amplifier and ADC 42, using a shift register or another kind of digital buffer. It may also be obtained by controlling a triggering time for the beginning of an ADC operation. In this regard, it may be noted that various solutions, possibly different from the ones presented above, can be considered to implement such a controllable delay upon emission and/or upon reception. In particular, the control of the temporal offset upon emission and/or upon reception, could be achieved by the U/S front end itself (depending on an adjustment signal received), instead of being achieved by the control module 20.

Anyhow, both the temporal offset upon emission $\delta t_{TX}$ and the temporal offset upon reception $\delta t_{RX}$ are offsets with respect to a (same) stable temporal reference, such as a clock signal, which is independent of the transducer's displacement.

The electronic unit 10 is configured to adjust the temporal offset upon emission $\delta t_{TX}$ and the temporal offset upon reception $\delta t_{RX}$ so as to compensate for temporal shifts of the echo signals received, with respect to the other, caused by the displacement of the ultrasound transducer 6 occurring during the sequence of ultrasound pulses emissions.

Indeed, as represented in FIG. 5, as the transducer 6 moves during the measurement, the distance (and so, the time of flight) between the U/S transducer and an element located at a given depth z within the tissue varies depending on the moment considered. FIG. 5 represents schematically, in the form of a chronogram, the displacement of the U/S transducer 6 and the times of emission of the U/S pulses or groups (e.g.: pairs) of pulses, during a typical transient elastography measurement. In this example, the pulse repetition frequency (of the group of pulses repetition frequency) is 500 Hz, while the transient vibration imparted to the transducer is a one-period of sinusoid having a duration of 20 ms and a peak-to-peak amplitude of 2 mm.

Figure 8:
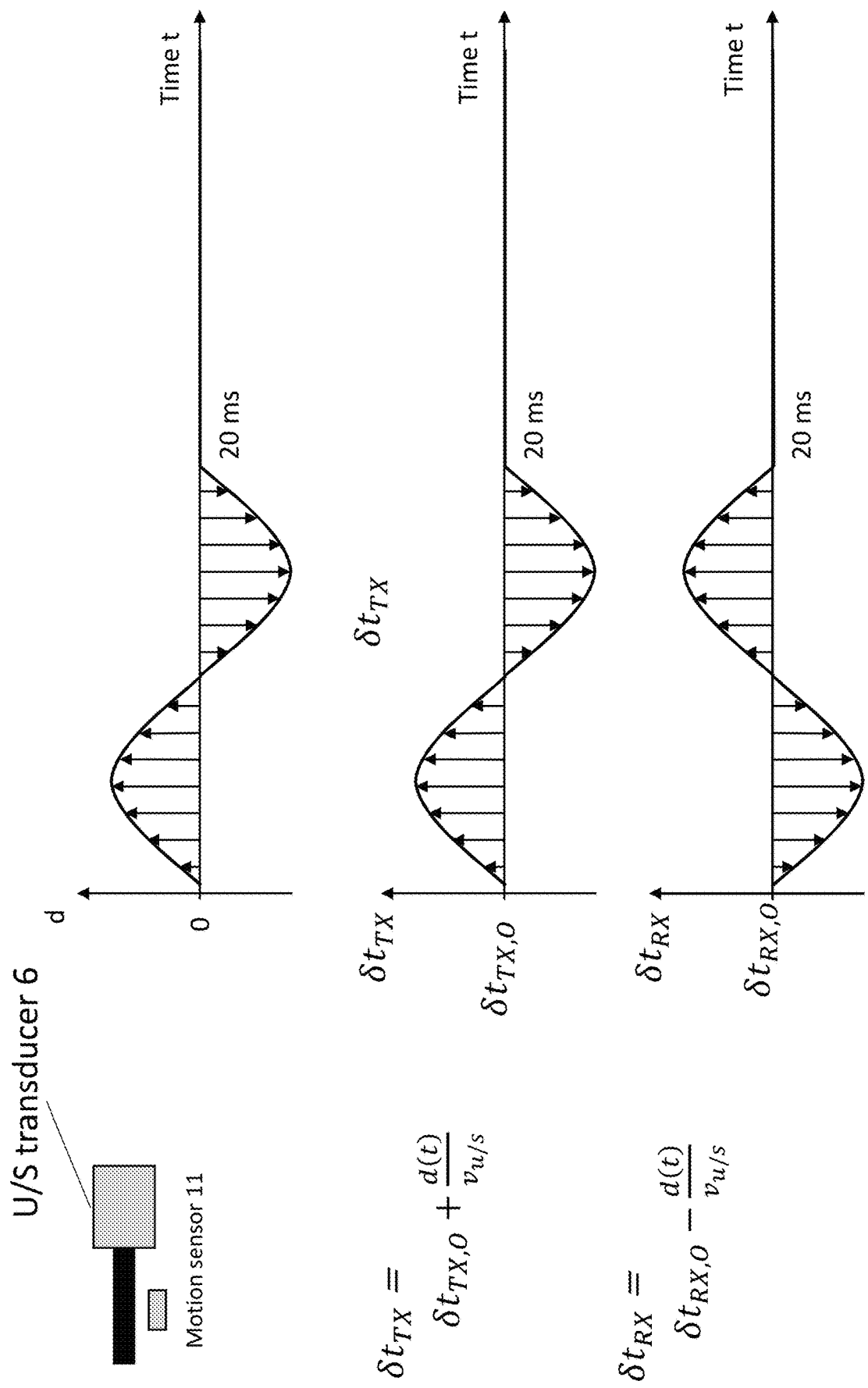
FIG. 8 schematically represents temporal offsets upon emission and upon reception generated by the electronic unit of FIG. 7, based on a transducer's displacement.

Here, as represented in FIGS. 7 and 8, the electronic unit 10 is configured more particularly:

to adjust the temporal offset upon emission $\delta t_{TX}$ so that it is equal to $\delta t_{TX,o}+d/v_{us}$, $\delta t_{TX,o}$ being a constant delay upon emission, and to adjust the temporal offset upon reception, so that it is equal to $\delta t_{RX,o}-d/v_{us}$, $\delta t_{RX,o}$ being a constant delay upon reception.

Here, the difference $\Delta t = \delta t_{RX} - \delta t_{TX}$ between these two temporal offsets is equal to the delay $\Delta t$ between the emission of one of the U/S pulses emitted, and the start of the echo signal recorded in response (these temporal offsets being two temporal offsets relative to a same temporal reference, or clock). This time difference $\Delta t$ is then equal to $\Delta t_o - 2 \cdot d/v_{us}$ with $\Delta t_o = \delta t_{RX,0} - \delta t_{TX,0}$.

The constant delay upon emission $\delta t_{TX,o}$ may be set, depending on the maximum displacement expected for the transducer, so that the $\delta t_{TX}$ remains positive. If a maximum peak-to-peak displacement amplitude of 2 mm (1 mm towards the tissue, and 1 mm backward) is expected, for instance, $\delta t_{TX,o}$ may be chosen higher than 0.7 µs (should the speed of ultrasound in the tissue be equal to 1.5 mm/µs). Regarding the constant delay upon emission $\delta t_{RX,o}$, it may be set so that $\Delta t_o = 2 \cdot z_{min}/v_{us}$.

As represented in FIG. 7, a correction module 21 determines the variable delay $d/v_{us}$, from the digitalized signal outputted by the signal conditioning module 32 (digitalized signal which is representative of the signal outputted by the displacement sensor 11). In this embodiment, the displacement d of the transducer 6 is its displacement relative to the probe's casing 3. The correction module 21 includes electronic circuitry to determine the variable delay $d/v_{us}$. This displacement corresponds to the displacement of the transducer 6 relative to a reference position of the transducer. This reference position is for instance the position of the transducer (position relative to the casing) when the probe is held against the subject's body, just before triggering the elastography measurement. It may also be an average position of the transducer, in the case of harmonic elastography. The value of d (which is an algebraic value, that can be either positive or negative) increases when the ultrasound transducer moves towards the tissue (towards the body of the subject); d corresponds to a variation of position along the axis z, directed towards the tissue.

As explained in the section entitled "summary", shifting temporally the emission and reception in this way, depending on the displacement d of the U/S transducer 6 at the time of emission, enables one to compensate for a temporal mis-alignment between echo signals caused by the displacement of the transducer during the acquisition of this series of echo signals.

Thanks to this delay compensation, the different echo signals recorded are temporarily re-aligned with each other. It means that, in each echo signal, the portion of the echo signal at a time given t after the beginning of the echo signal corresponds to the same depth z in the medium (i.e.: corresponds to the signal backscattered by the portion of the tissue located at the same depth z in the medium), for the different echo signals.

The electronic unit 10 may also be configured:
  to correlate the echo signals recorded (these echo signals having been re-aligned temporally prior to this correlation), to determine the tissue displacement as a function of depth z, for each time t (that is: step c) mentioned above in the "background" section), and
  to compute the z-derivative $\partial */\partial z$ of the spatio-temporal displacement map thus obtained (to remove possible residual, un-compensated small z-shifts that may remain due to a non-completely perfect compensation of the transducer's displacement).

In the case of FIG. 7, the temporal offsets upon emission and reception $\delta t_{TX}$ and $\delta t_{RX}$ are adjusted so as to be equal to $\delta t_{TX,o} + d/v_{us}$ and $\delta t_{RX,o} - d/v_{us}$ respectively.

Still, in an alternative, these temporal offsets could be adjusted differently, as long as their difference $\Delta t = \delta t_{RX} - \delta t_{TX}$ varies as a function of $2 \cdot d/v_{us}$.

For instance, the compensation could be achieved entirely upon emission, $\delta t_{TX}$ being then adjusted so as to be equal to $\delta t'_{TX,o} + 2 \cdot d/v_{us}$, while $\delta t_{RX}$ would remain constant over time (no adjustment upon reception).

Conversely, the compensation could be achieved entirely upon reception, $\delta t_{RX}$ being then adjusted so as to be equal to $\delta t'_{RX,o} - 2 \cdot d/v_{us}$, while $\delta t_{TX}$ would remain constant over time (no adjustment upon emission).

More generally, the electronic unit 10 could be configured:
  to adjust the temporal offset upon emission $\delta t_{TX}$ so that it is equal to $\delta t_{TX,o} + C \cdot d/v_{us}$, and
  to adjust the temporal offset upon reception, so that it is equal to $\delta t_{RX,o} - (2-C) \cdot d/v_{us}$, C being a constant coefficient between 0 and 2.

The case presented above, with reference to FIGS. 7 and 8, corresponds to C=1. In this case, the overall time-shift correction to be applied (that is $-2 \cdot d/v_{us}$) is distributed evenly between the temporal offset upon emission and the temporal offset upon reception. As explained in the section "summary", this specific correction is optimal, in terms of time-sampling accuracy of the tissue deformations.

Figure 9:
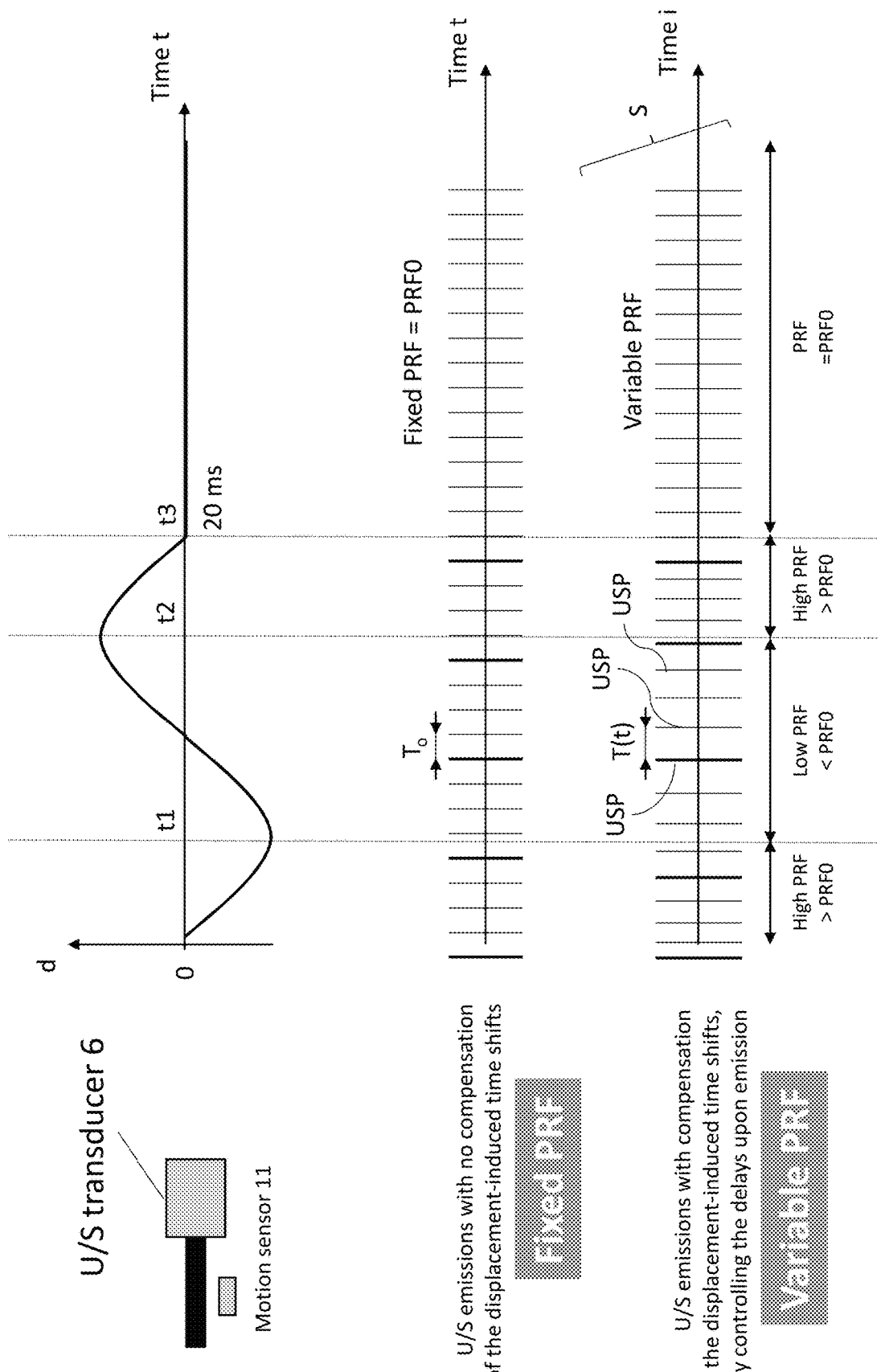
FIG. 9 schematically represents a sequence of ultrasound pulses emitted over time by the device of FIG. 6, during a typical elastography measurement.

FIG. 9 represents schematically the sequence S of U/S pulses emitted by the device 1 presented above (chronogram b)), for an example of displacement d(t) of the U/S transducer 6. It also represents the sequence $S_o$ that would have been emitted without displacement (chronogram a)). In this example, in the un-delayed, reference sequence $S_o$, the U/S pulses are repeated periodically, regularly, with a constant Pulse Repetition Frequency PRF0. The pulse repetition period, that is, the duration between any of these pulses and the pulse immediately after it, is then noted To and is constant. In contrast, in the sequence emitted by device 1, the pulse repetition period T is not constant over time, as can be seen in FIG. 9.

This variation of the time lapse between two pulses is a consequence of the delays upon emission applied to the two pulses considered, delays that are different for these two pulses as the value of the displacement d(t) is different when the first pulse is emitted, and when the second one is emitted.

So, as illustrated in FIG. 9, when the U/S transducer 6 does not move (i.e.: when d(t) is zero, or constant), then, the pulse repetition frequency PRF is constant, equal to PRF0. But when the U/S transducer 6 moves towards the tissue (when d increases, which is the case between time t1 and time t2 in FIG. 9), then the pulse repetition frequency PRF is smaller than PRF0, and the pulse repetition period T is higher than To. Conversely, when the U/S transducer 6 moves backwards (when d decreases, which is the case between 0 and time t1, and between time t2 and time t3, in FIG. 9), then the pulse repetition frequency PRF is higher than PRF0, and the pulse repetition period T is smaller than To.

In the second embodiment of the elastography device, 1', instead of time-shifting the different pulses of a reference, un-delayed sequence So based on the displacement d, it is directly the pulse-repetition period T of the sequence generated which is adjusted, depending on the displacement d. The pulse-repetition period T is adjusted more specifically depending on the time-derivative of d, that is, depending on the speed of displacement of the U/S transducer $v = \dot{d} = d(d)/dt$.

In the second embodiment, the electronic unit 10' of the device 1', represented schematically on FIG. 10 as a block-diagram, is thus configured to generate the sequence of pulses to be emitted with a pulse repetition period T which is adjusted in real time, based on the displacement d at the time of emission, so that $T = T_o \times (1 + v/v_{us})$. As mentioned above, To is a base, reference repetition period. It is equal to the duration between two successive pulses when the U/S transducer 6 does not move. To may be constant over time, like in the case of FIG. 9.

As explained in the section "summary", adjusting the pulse repetition period T in this way produces the same result, or substantially the same result as adjusting the temporal offset upon emission the temporal offset upon emission $\delta t_{TX}$ so that it is equal to $\delta t_{TX,o}+d/v_{us}$ (like in the case of the first embodiment). Indeed, adjusting the pulse repetition period T in this way is equivalent, or substantially equivalent to adjusting the time-derivative of the offset upon emission $\delta t_{TX}$ depending on the time-derivative of d, instead of adjusting the offset itself based on d.

The different elements of the device 1' according to the second embodiment (device which is represented partially in FIG. 10) are identical or at least similar to those of the device 1 of the first embodiment, except that the electronic unit 10' is configured differently regarding the U/S pulses emission control (as it is configured to adjust the pulse repetition period upon emission depending on d, instead of adjusting each temporal offset upon emission depending on d).

More specifically, in the device 1' according to the second embodiment, the probe 2 and the central unit 7 may be identical those of the device 1 of the first embodiment, except that the control module 20' is arranged differently. The controllable delay 23 of the first embodiment is replaced by a controllable U/S pulses sequence generator 23' which generates the signal that controls the U/S pulser 41, based on the displacement d of the U/S transducer 6. This signal is generated so that the pulse repetition period T within this signal is equal to $T_o \times (1+v/v_{us})$.

Other electronic implementations, possibly different from the one presented above, can be considered to implement such a controllable pulse repetition period generation. In particular, the different functions of the electronic unit presented above being distributed differently among the elements and module of the device.

Besides, instead of being configured to adjust the pulse repetition period T so that it is equal to $T_o \times (1+v/v_{us})$, the electronic unit 10' could be configured:

to adjust T so that it is equal to $T_o \times (1+C \cdot v/v_{us})$, C being a constant coefficient between 0 and 2, and to adjust the temporal offset upon reception $\delta t_{RX}$ so that it is equal to $\delta t_{RX,o} - (2-C) \cdot d/v_{us}$.

As explained above about the first embodiment, the case C=1 is a case in which the overall time-shift correction to be applied (to compensate for the U/S transducer displacement) is distributed evenly between emission and reception, which is optimal, in terms of time-sampling accuracy of the tissue deformations.

Still, other cases also enable to compensate for most of the effects of the movement of the U/S transducer.

For instance, the compensation could be achieved entirely upon emission, the pulse repetition period T being adjusted so that it is equal to $T_o \times (1+2 \cdot v/v_{us})$ while $\delta t_{RX}$ would remain constant over time (no adjustment upon reception), which corresponds to C=2.

In the example presented above, the U/S pulses are transmitted one at a time, two successive pulses being separated by $T_o$ when there is no transducer's motion. Still, the pulse repetition period adjustment technique presented above can also be applied to other kinds of U/S pulses sequences. For instance, the un-delayed, reference sequence $S_o$ could be composed of pairs of pulses (more generally, groups of pulses), repeated periodically, with a period $T_o$ between two successive pairs of pulses and a duration $t_{intra}$ between the two pulses of each pair. In such a case, the pulse repetition period is adjusted depending on d, as described above, and the quantity $t_{intra}$ is also multiplied by the correcting factor $(1+C \cdot v/v_{us})$, just as To. More generally, all the temporal patterns of the U/S base sequence So, which are repeated periodically, are temporally expanded (or reduced, depending on the sign of v) by the factor $(1+C \cdot v/v_{us})$.

FIG. 11 represents schematically the elastography device 1" according to the third embodiment. As mentioned above, in this embodiment, the U/S transducer 6 is bound to the probe casing 3 with no motion with respect to the probe casing. The U/S transducer 6 is fixed at an end oh the tip 4", which is fitted to the casing 3 with no motion with respect to the casing. The probe 2" comprises a mass 12 arranged so that it can move with respect to the casing, along the axis z of the casing. The tip 4" and the U/S transducer 6 are centered onto this axis. The vibrator 5", the mass 12 and the U/S transducer 6 are rotationally symmetrical around the axis z. The vibrator 5" is arranged to move the mass 12 with respect to the casing (or, in other words, to move the casing 3 with respect to the inertia mass 12), to make the whole probe moving towards the tissue and back, by virtue of a recoil effect. This inertial probe 2" is similar to the one described in the patent n°EP3315074 by Sandrin and Audière.

In this embodiment, the displacement sensor 11" is an inertial sensor, fitted to the probe, with no motion with respect to the probe, and so, with no motion with respect to the U/S transducer 6. The measurement signal outputted by the displacement sensor 11" is thus representative of the displacement of the single ultrasound transducer 6 relative to an inertial frame of reference (this frame of reference being the one associated to the room or the place where the measurement is carried on). The displacement sensor 11" is an accelerometer, for instance a MEMS accelerometer.

In this third embodiment, the electronic unit is identical, or at least similar to the electronic unit 10 of the first embodiment (see FIG. 7), except that it comprises a double temporal integrator, to convert the acceleration signal into a position signal.

One may note that, in the third embodiment, the displacement d is a kind of absolute displacement, while in the first and second embodiment, it a kind of relative displacement (namely, the transducer's displacement with respect to the probe's casing).

So, in the third embodiment, the displacement d taken into account to adjust the temporal offsets upon emission and/or reception corresponds exactly, or almost exactly to the actual displacement of the U/S transducer relative to the body of the subject (as the subject is at rest, during such an examination). In this case, the time-shifts compensation is thus optimal, in principle (if one assumes that the measurement is not impaired by biases or noises).

In the first and second embodiments, even if the displacement taken into account is only the displacement relative to the probe, it turns out that an adequate time-shift compensation is obtained, in fact. It may seem quite surprising, at first glance. Indeed, in the first and second embodiments, then the vibrator pushes the tip towards the subject, a slight recoil of the probe is usually observed, even if the probe is firmly held. And so, the displacement of the transducer 6 relative to the probe's casing, which is the quantity taken into account to compensate for the times-shifts, does not match exactly the displacement of the transducer with respect to the subject's body (which should be the one taken into account, ideally).

An explanation for the fact that both techniques (either measuring the absolute displacement by means of an inertial sensor, or measuring the displacement relative to the casing) lead to adequate results is that that electronic unit is configured, in both cases, to compute the z-derivative $\partial*/\partial z$ of the spatio-temporal displacement map finally obtained (obtained by correlating the echo signals re-aligned using the technique mentioned above). So, even if the compensation of the displacement of the transducer is not entirely exact (either because of the probe recoil mentioned above, or because of the noise and/or biases of the displacement deduced form the signal provided by the inertial sensor), possible residual, un-compensated small z-shifts are removed by the z-derivative. In other words, the main goal of the time-shift compensation is in fact to remove most of the displacement-induced time shift (which is achieved both in the first and third embodiment), to avoid having to compute correlations for echo signals with big, constant offsets between echo signals (which would be time-consuming, and which would increase the noise impairing the result).

From the foregoing, it will be appreciated that specific embodiments of the invention have been described herein for purposes of illustration, but that various modifications may be made to the device presented above, in addition to those already mentioned.

For instance, the probe could comprise several U/S transducers, instead of just one. In this case, all ultrasound transducers of the probe that are arranged to emit ultrasound pulses in the tissue to be characterized are motionless with respect to each other, as already mentioned. These transducers may be distributed symmetrically with respect to each other, with respect to the probe axis z, so that the rotational symmetry of the probe is preserved. They could also be distributed regularly around this axis, instead of being exactly symmetrical with respect to each others.

Besides, in the case of the first and second embodiment (transducer movable with respect to the casing), the displacement sensor could also be an inertial sensor, fixed onto the shaft 40, for example. Alternatively, the device could comprise both an inertial sensor, motionless with respect to the casing, and a displacement sensor like the sensor 11 described above (both sensors being employed to determine the transducer's displacement relative to the subject's body).

In another embodiment, the displacement d(t) of the transducer could be deduced from the command signal controlling the vibrator, instead of being deduced form the measurement signal $S_d$.

In an alternative embodiment, the displacement d(t) of the transducer, taken into account to compensate for the displacement-induced time-shift, could be obtained by reading pre-recorded displacement data stored in a memory of the device. This displacement data may be obtained by acquiring a signal representative of the transducer displacement during a typical elastography measurement sequence. This displacement data could be acquired during a preliminary test phase, during which the device is tested and characterized. Using such pre-recorded data (instead of measuring the transducer displacement on-the-fly, each time an elastography measurement is triggered again) enables a reliable time-shift compensation, in particular when the vibrator is controlled by means of a control loop (indeed, in such a case, the displacement obtained is the same or at least similar for each elastography measurement carried on—thanks to the control loop—and so, the same, pre-recorded displacement signal can be employed).

The time-shift compensation technique presented above has been described in detail in the case of Vibration-Controlled Transient Elastography, but it may be applied as well to Vibration-Controlled Harmonic Elastography, such as described in the patent application published as EP3769691, for instance.

It will be appreciated that the various embodiments described previously are combinable according to any technically permissible combinations.

The invention claimed is:

1. An elastography device comprising:
   a probe, to be held against the body of a subject, the probe comprising:
   a single ultrasound transducer; or a plurality of ultrasound transducers, all ultrasound transducers of the probe being motionless with respect to each other, and
   a low frequency vibrator arranged to induce a displacement of said single ultrasound transducer or plurality of ultrasound transducers towards a tissue to be characterized, and
   an electronic unit comprising an electronic circuit, configured to control the single ultrasound transducer or plurality of ultrasound transducers to emit a sequence of ultrasound pulses in said tissue to be characterized, and configured to acquire echo signals received by the single ultrasound transducer or plurality of ultrasound transducers in response to the sequence of tracking ultrasound pulses emitted, in order to track how elastic waves travel in said tissue, said elastic waves being induced in the tissue by the displacement of the single ultrasound transducer or the plurality of ultrasound transducers,
   the electronic unit being configured to generate ultrasound pulses at a variable pulse repetition frequency during the displacement of said single ultrasound transducer or plurality of ultrasound transducers to track how said elastic waves travel in said tissue such that a temporal duration between two successive ultrasound pulses varies in said sequence of ultrasound pulses.

2. The elastography device of claim 1, wherein said sequence of ultrasound pulses includes a first temporal sequence of a first plurality of ultrasound pulses that are emitted at a first pulse repetition frequency and a second temporal sequence of a second plurality of ultrasound pulses that are emitted at a second pulse repetition frequency, which is different from the first frequency.

3. The elastography device of claim 2, wherein the first pulse repetition frequency is variable and the second pulse repetition frequency is fixed.

4. The elastography device of claim 2, wherein said sequence of ultrasound pulses includes a third temporal sequence of a third plurality of ultrasound pulses that are emitted at a third pulse repetition frequency, which is different from the first and the second pulse repetition frequency.

5. The elastography device of claim 2, wherein the first plurality of ultrasound pulses are emitted when the single ultrasound transducer or plurality of ultrasound transducers move towards said tissue to be characterized and wherein the second plurality of ultrasound pulses are emitted when the single ultrasound transducer or plurality of ultrasound transducers move away from said tissue to be characterized.

6. The elastography device of claim 5, wherein the first pulse repetition frequency is lower than the second pulse repetition frequency.

7. The elastography device of claim 2, wherein the first and/or second temporal sequences are repeated in said sequence of ultrasound pulses.

8. The elastography device of claim 1, wherein the variable pulse repetition frequency varies in the range from 1 Hz to 500 Hz during emission of the sequence of ultrasound pulses in said tissue to be characterized and acquisition of said echo signals.

9. The elastography device of claim 1, wherein the single ultrasound transducer or plurality of ultrasound transducers is/are movable relative to a casing in which the low frequency vibrator is arranged.

10. The elastography device of claim 1, wherein the variable pulse repetition frequency is selected to compensate for a temporal shift of an echo signal with respect to other echo signals acquired, caused by the displacement of the ultrasound transducer or plurality of ultrasound transducers occurring during said sequence of ultrasound pulses.

11. The elastography device of claim 1, wherein a temporal offset upon emission of the ultrasound pulses is adjusted so that a difference thereof varies as a function of $2 \cdot d/v_{us}$, where d is the displacement of the single transducer or plurality of ultrasound transducers at the time of emission, and where $v_{us}$ is the speed of ultrasound in said tissue.

12. An elastography method, implemented by a device that includes a probe including
a single ultrasound transducer; or a plurality of ultrasound transducers, all ultrasound transducers of the probe being motionless with respect to each other, and
a low frequency vibrator, arranged to induce a displacement of said ultrasound transducer or plurality of ultrasound transducers towards a tissue to be characterized,
the method comprising:
controlling the low frequency vibrator to induce the displacement of said ultrasound transducer or plurality of ultrasound transducers towards said tissue, and
controlling said ultrasound transducer or plurality of ultrasound transducers to emit a sequence of ultrasound pulses in the tissue to be characterized, and acquiring echo signals received by the ultrasound transducer or plurality of ultrasound transducers in response to the sequence of ultrasound pulses emitted, to track how elastic waves travel in the tissue, the elastic waves being induced in the tissue by the displacement of the ultrasound transducer or plurality of ultrasound transducers, travel in the tissue,
wherein ultrasound pulses are generated at a variable pulse repetition frequency during the displacement of said single ultrasound transducer or plurality of ultrasound transducers to track how said elastic waves travel in said tissue such that a temporal duration between two successive ultrasound pulses varies in said sequence of ultrasound pulses.

13. The elastography method of claim 12, wherein said sequence of ultrasound pulses includes a first temporal sequence of a first plurality of ultrasound pulses that are emitted at a first pulse repetition frequency and a second temporal sequence of a second plurality of ultrasound pulses that are emitted at a second pulse repetition frequency, which is different from the first frequency.

14. The elastography method of claim 13, wherein the first pulse repetition frequency is variable and the second pulse repetition frequency is fixed.

15. The elastography method of claim 13, wherein said sequence of ultrasound pulses includes a third temporal sequence of a third plurality of ultrasound pulses that are emitted at a third pulse repetition frequency, which is different from the first and the second pulse repetition frequency.

16. The elastography method of claim 13, wherein the first plurality of ultrasound pulses are emitted when the single ultrasound transducer or plurality of ultrasound transducers move towards said tissue to be characterized and wherein the second plurality of ultrasound pulses are emitted when the single ultrasound transducer or plurality of ultrasound transducers move away from said tissue to be characterized.

17. The elastography method of claim 16, wherein the first pulse repetition frequency is lower than the second pulse repetition frequency.

18. The elastography method of claim 13, wherein the first and/or second temporal sequences are repeated in said sequence of ultrasound pulses.

19. The elastography method of claim 12, wherein the variable pulse repetition frequency varies in the range from 1 Hz to 500 Hz during emission of the sequence of ultrasound pulses in said tissue to be characterized and acquisition of said echo signals.

20. The elastography method of claim 12, wherein the single ultrasound transducer or plurality of ultrasound transducers is/are movable relative to a casing in which the low frequency vibrator is arranged.

\* \* \* \* \*